United States Patent [19]
Soya et al.

[11] Patent Number: 5,864,382
[45] Date of Patent: Jan. 26, 1999

[54] OPTHALMIC APPARATUS FOR ANALYZING A SECTION OF AN ANTERIOR PART OF AN EYE

[75] Inventors: Koichi Soya, Kawasaki; Hirohiko Hanaki, Gamagori, both of Japan

[73] Assignee: Nidek Company, Ltd., Japan

[21] Appl. No.: 896,587

[22] Filed: Jul. 18, 1997

[30] Foreign Application Priority Data

Jul. 25, 1996 [JP] Japan ................................. 8-215055

[51] Int. Cl.$^6$ .................................................. A61B 3/14
[52] U.S. Cl. .......................................... 351/206; 351/221
[58] Field of Search ................................. 351/205, 206, 351/221, 213, 214, 200, 246, 208; 354/62

[56] References Cited

U.S. PATENT DOCUMENTS

| | | | |
|---|---|---|---|
| 5,202,708 | 4/1993 | Sasaki et al. | 351/206 |
| 5,347,331 | 9/1994 | Isogai et al. | 351/206 |
| 5,381,194 | 1/1995 | Nishio et al. | 351/208 |
| 5,436,679 | 7/1995 | Ohtsuka et al. | 351/206 |

OTHER PUBLICATIONS

"Reproducibility of Data Obtained by a Newly Developed by a Newly Developed Anterior Eye Segment Analysis System, EAS–1000", by Yasuo Sakamoto et al. Ophthalmic Research, 1992; 24(suppl 1):10–20.

*Primary Examiner*—Hung Xuan Dang
*Attorney, Agent, or Firm*—Rossi & Associates

[57] ABSTRACT

An ophthalmic apparatus for analyzing a section of an anterior part of an eye providing an input device for inputting a photographed image data of corneal section which is cut optically by a slit light, an image memory for memorizing the image data of corneal section inputted by the input device, an image analyzing device for analyzing an optical density of the image of corneal section by processing the image data of corneal section memorized by the image memory, and a display device for displaying an analyzed result of the image analyzing device.

16 Claims, 4 Drawing Sheets

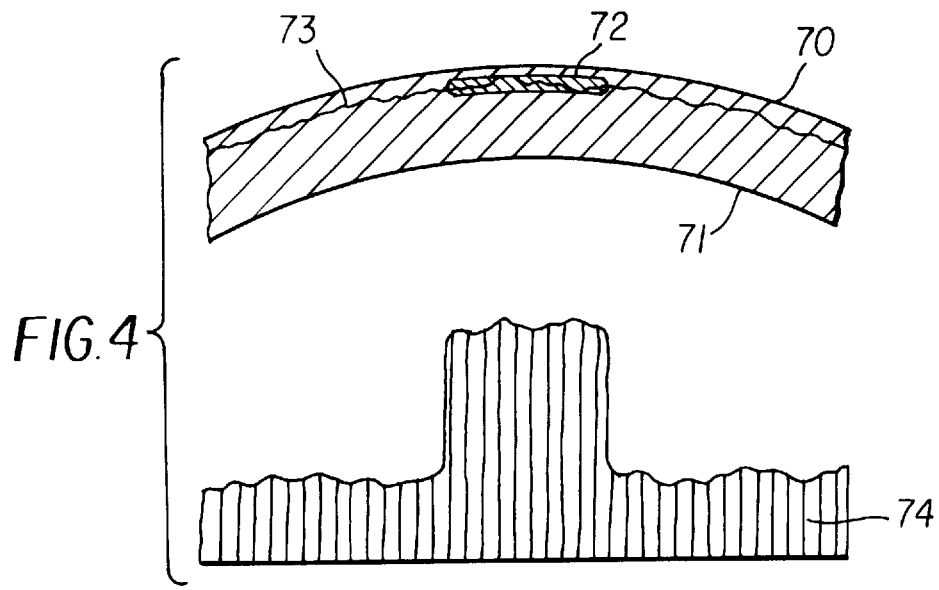
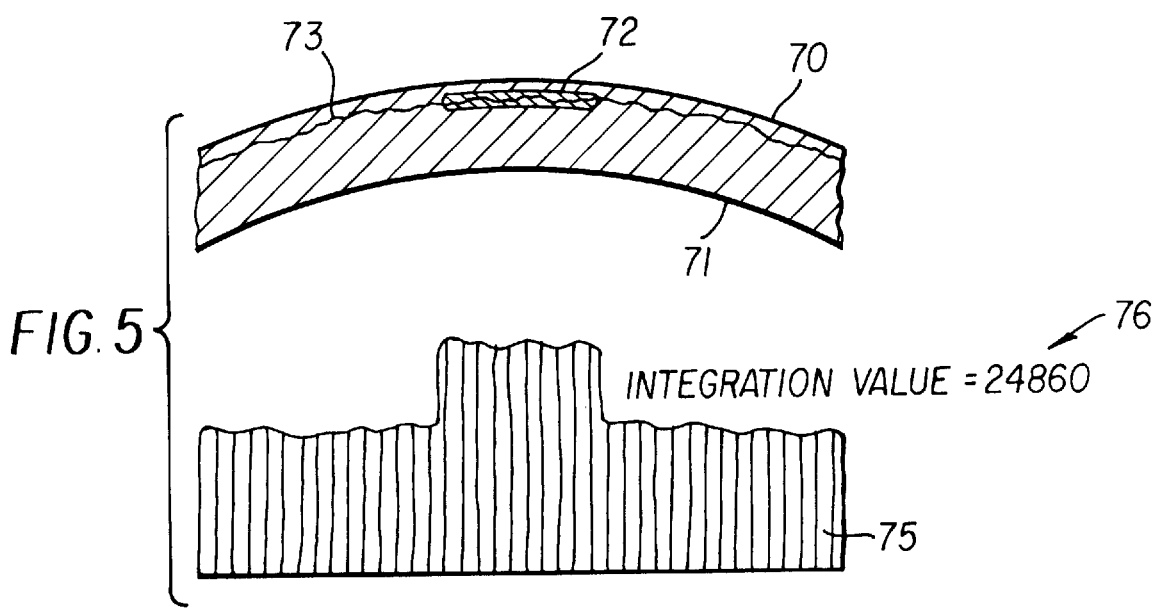

OPTHALMIC APPARATUS FOR ANALYZING A SECTION OF AN ANTERIOR PART OF AN EYE

BACKGROUND OF THE INVENTION

1. Field of the Invention

This present invention relates to an ophthalmic apparatus for analyzing a section of an anterior part of an eye, and more particularly relates to the ophthalmic apparatus for analyzing an opacification condition of a cornea by processing an image of corneal section.

2. Description of Related Art

Recently, a corneal operation has been well-known in order to correct ametropia of an eyeball by ablating a corneal surface with using excimer laser beam so as to change a corneal curvature. This sort of operation may cause hypodermic opacification of epitherium anterius corneae after the operation.

Usually, in case that the hypodermic opacification of the epitherium anterius corneae is caused, a slit-light lamp used to be applied for the examination. An operator observed a corneal section which was optically cut by the slit light by using an observing microscope so as to estimate the opacification level, the condition of a convergent heal, and the like.

However, the operator tended to depend on his own subjective judgement when the hypodermic opacification of the epitherium anterius corneae was estimated. Even though the same estimated standard is applied, it resulted in an disadvantage that each individual different level of operator effected on the estimation. Also, it is difficult to estimate only by observation.

SUMMARY OF THE INVENTION

The present invention has been made in view of the above circumstance and has an object to overcome the above problem and to provide an ophthalmic apparatus for analyzing a section of an anterior part of an eye, capable of defining a portion of corneal opacification by the image of corneal section, and capable of quantifying the opacification condition so as to achieve the accurate estimation.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus for analyzing a section of an anterior part of an eye comprises input means for inputting a photographed image data of corneal section which is cut optically by a slit light, image memory means for memorizing the image data of corneal section inputted by the input means, image analyzing means for analyzing an optical density of the image of corneal section by processing the image data of corneal section memorized by the image memory means; and display means for displaying an analyzed result of the image analyzing means.

In another aspect of the present invention, the ophthalmic apparatus providing a photographing unit for a corneal section and an image analyzing unit, the photographing unit including at least slit projection optical system for projecting a slit image onto an eye to be examined, and slit-section photographing optical system for photographing an optical sectional image of the slit image which is projected onto the eye to be examined by the slit projection optical system, the image analyzing unit including input means for inputting the image data of a section of an anterior part of an eye photographed by the slit-section photographing optical system, first analyzing means for analyzing a point coordinate and an optical density of a direction which intersects on a slit-light projection optical axis of the slit photo-image of the eye to be examined photographed by the slit-section photographing optical system based on the image data of the section of the anterior part of the eye which is inputted by the input means and second analyzing means for analyzing the peak optical density and its point coordinate of the axial direction of the slit-light projection of the slit-light photo-image.

As described above, according to the present invention, the apparatus enables to define the portion of corneal opacification by the image of corneal section, and enables to achieve the estimation of opacification accurately, because the opacification condition can be obtained by quantifying the opacification condition in the whole direction of depth of the cornea.

BRIEF DESCRIPTION OF THE DRAWING

The accompanying drawings, which are incorporated in and constitute a part of this specification, illustrate embodiments of the present invention and, together with the description, serve to explain the objects, advantages and principles of the invention.

In the drawings,

FIG. 4 is a view showing a display sample when a first analyzing mode is selected.

FIG. 5 is a view showing a display sample when a second analyzing mode is selected.

DETAILED DESCRIPTION OF THE PREFERRED EMBODIMENTS

Figure 1:
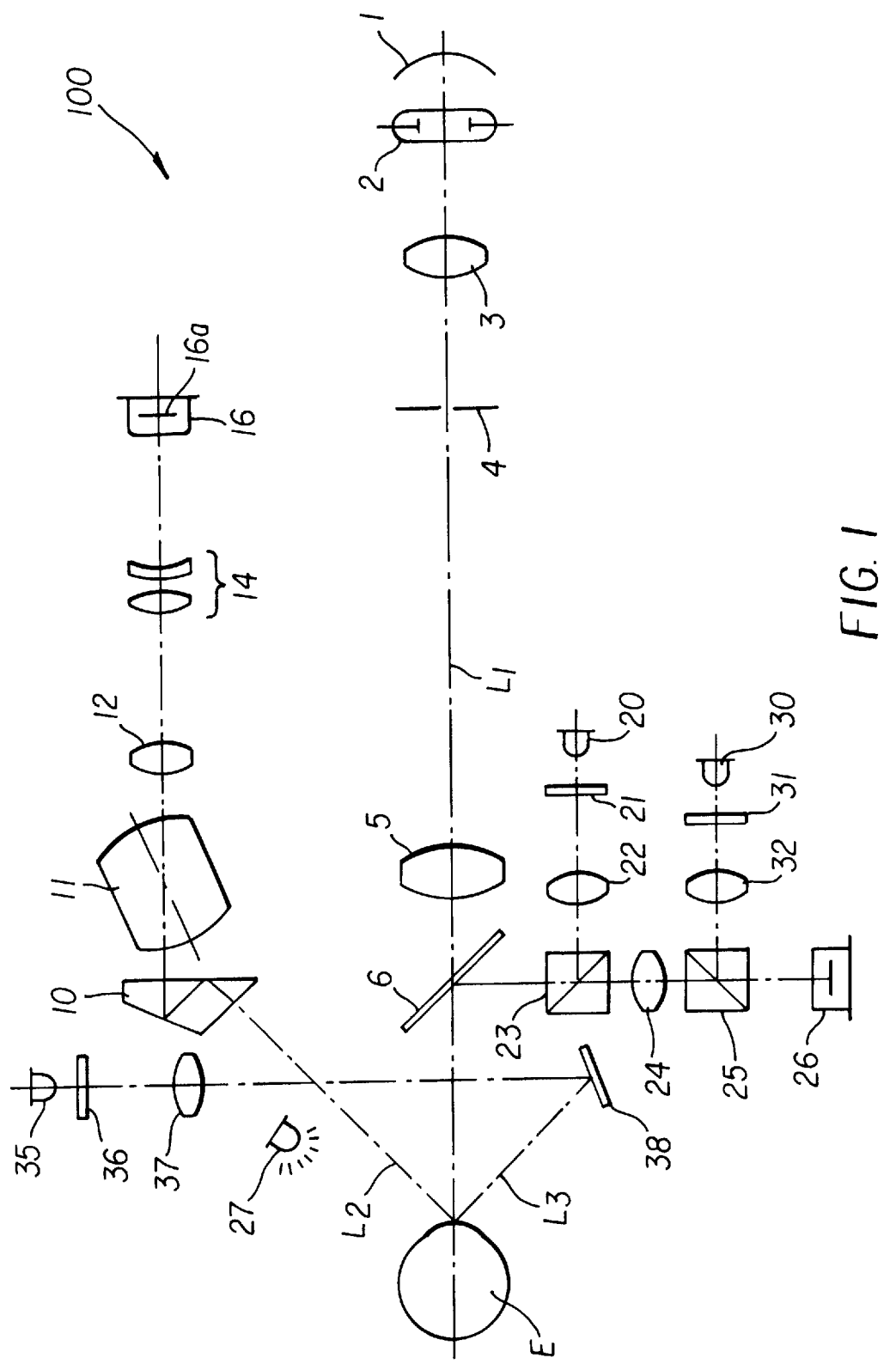
FIG. 1 is a view showing a constitution of optical system of a photographing unit 100 for a corneal section in the embodiment of the present invention.

A detailed description of one preferred embodiment of an ophthalmic apparatus for analyzing a section of an anterior part of an eye embodying the present invention will now be given referring to the accompanying. FIG. 1 is a view showing a constitution of optical system of a photographic unit 100 of the preferred embodiment in order to obtain the image of corneal section.

(Slit-Light Projection System)

Reference numeral 1 denotes a reflecting mirror, 2 is a flash lump for photography, 3 is a condenser lens, 4 is a slit aperture diaphragm, 5 is a projection lens, and 6 is a dichroic mirror which is placed slantingly on an optical axis $L_1$ of the slit-light projection optical system. The dichroic mirror 6 has a characteristic of transmitting most of visible light and of reflecting infrared-light.

A luminous flux emitted from the flash lump 2 is collected by the condenser lens 3, thereby the slit aperture diaphragm 4 is illuminated. The luminous flux which is formed to be a slender slit-shape by the slit aperture diaphragm 4 is transmitted through the projection lens 5 and the dichroic mirror 6 so as to be projected onto an eye E to be examined and a slit image of the slit aperture diaphragm 4 is projected on the anterior part of the eye E. By this process, an optic media of the anterior part of the eye (such as a cornea and a crystalline lens) is illuminated under the state of being cut optically by a white light within a range of visible level. Incidentally, the photography is performed by applying a scattering light from biomolecule of the cornea and the crystalline lens of the eye which are cut optically. Therefore, if the wavelength becomes shorter, the scatter may be greater and a capacity for detecting may increase. However, it may be desirable to use a moderate white light, because an optical toxicity would be more harmful to the eyeball within a range of ultraviolet level.

(Slit-Section Photographing Optical System)

Reference numeral $L_2$ denotes a photographic optical axis of the slit-section photographing optical system. Reference numeral 10 is a deflection angle prism for changing a direction of the photographic optical axis $L_2$. Reference numeral 11 is a photographic lens, 12 is an image-forming lens for use in photomacrography, 14 is an anamorphic lens, and 16 is a CCD camera. The photographic optical axis $L_2$ is provided so as to intersect the optical axis $L_1$ at adjacent to the vertex of cornea, also an inclination angle of each optical axis is 45-degrees angle. The photographic lens 11 is arranged slantingly corresponding to the photographic optical axis of which direction is adjustable by the deflection angle prism 10 so as to fulfill Scheimpflug's principle. That is, when the deflection angle prism 10 is not used, a cross line which the extension of optical section of the anterior part of the eye by the slit illumination light intersects the extension of a photographic image 16a of the CCD camera 16 is placed so as to intersect on the extension of a principle place of the photographic lens 11. According to this optical arrangement, a sectional image photographed by the CCD camera 16 (a sectional image of slit-light which is formed by the scattering light from the biomolecule of the anterior part of the eye around the center of a collective point of slit-light) can hold a focal depth for focusing the approximate entirety of its sectional images.

(First Alignment Target Projection Optical System)

Reference numeral 20 denotes a light source for the first alignment for projecting an alignment target from the front side of the eye (from a direction of visual axis), and then an infrared-light partly including visible light is emitted for sharing with a fixation light source. Reference numeral 21 is a target plate having a pin-hole aperture on a projection optical axis, and 22 is a projection lens The target plate 21 is positioned at adjacent to the front focusing distance of the projection lens 22. Reference numeral 23 denotes a beam splitter. The target plate 21 is illuminated by a light emitted from the light source 20. After an alignment light emerged from the target plate 21 is formed to a parallel luminous flux by the projection lens 22, the alignment light is reflected at the beam splitter 23. Thereafter, the alignment light is reflected at the dichroic mirror 6 so as to be forwarded toward the eye E alongside of the optical axis $L_1$. As a result, by a surface reflection of cornea, an target image of the target plate 21 is formed at the position of interocular side only for a half distance of the radius of corneal curvature from the vertex of cornea. Also, since the light source partly includes the visible light, the first alignment target projection optical system combines a fixation optical system, thereby the fixation target by the pin-hole aperture of the target plate 21 is fixated onto the eye.

(Front Photographing Optical System for an Anterior Part of an Eye)

Reference numeral 24 denotes a photographic lens, 25 is a beam splitter, and 26 is a CCD camera for observing the front side having a sensitivity within a range of infrared level. Reference numeral 27 is a light source for an infrared-illumination to illuminate the anterior part of the eye. After a partial luminous flux reflected at a cornea among alignment luminous fluxes projected by the first alignment target projection optical system is reflected at the dichroic mirror 6, it is passed through the beam splitter 23, the photographic lens 24, and the beam splitter 25 so as to be photographed by the CCD camera 26. Also, the anterior part image of the eye E illuminated by the illumination light source 27 is photographed by the CCD camera 26 passed through the same optical path.

(Front Reticle Optical System)

Reference numeral 30 is a illumination light source for a reticle-plate, 31 is a reticle plate that an aiming mark is formed, and 32 is a reticle projection lens. The aiming mark of the reticle plate 31 illuminated by the illumination light source 30 is reflected at the beam splitter 25 after passed through the reticle projection lens 32. Thereby, the aiming mark is photographed by the CCD camera 26 as well as the anterior part image of the eye and the target image.

(Second Alignment Target Projection Optical System)

Reference numeral 35 is a light source for the second alignment such a light emitting diode (a visible light or a laser diode or the like may be used as an alignment light), 36 is a target plate having a pin-hole aperture at the center of optical target axis, 37 is a projection lens, and 38 is a mirror.

A projection optical axis $L_3$ of the second alignment target projection system is placed within the same plane of the optical axis $L_2$. Also, the projection optical axis $L_3$ is provided so as to put the optical axis $L_1$ between the optical axis $L_2$ and $L_3$ and make the optical axis $L_2$ and $L_3$ symmetrical corresponding to the optical axis $L_1$ with each having a inclination angle of 45 degrees. The target plate 36 is illuminated by a light emitted from the light source 35, thereby a target illuminaus flux by the target plate 36 is reflected at the mirror 38 so that the target illuminaus flux is collected and projected onto the eye E from the oblique direction.

In the above-mentioned optical systems, the slit-section photographing optical system, the second alignment target projection optical system, the slit aperture diaphragm 4 and reticle optical system for photographing a section (a reticle for photographing a section is produced electrically in the preferred embodiment) are structured so as to rotate the optical system $L_1$ by a rotation mechanism not illustrated in this specification. Therefore, a section of any angle can be photographed.

Figure 2:
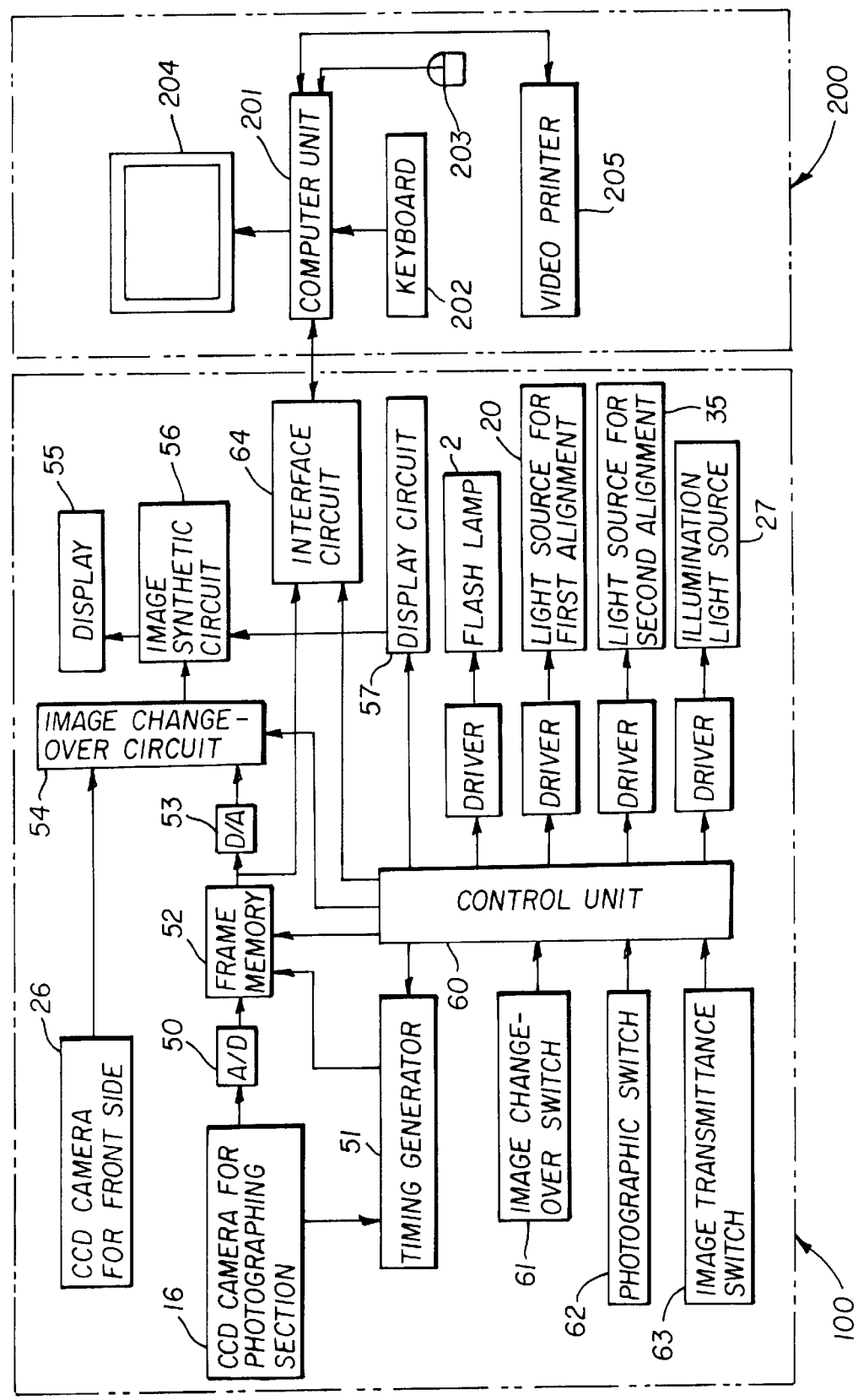
FIG. 2 is a view showing constitutions of electrical system of the photographing unit 100 for a corneal section and a picture analyzing unit 200 in the embodiment of the present invention.

FIG. 2 is a view showing constitutions of electrical system of the photographing unit 100 for a corneal section and a picture analyzing unit 200.

(Photographing Unit for a Corneal Section>

A video signal from the CCD camera 16 is digitized by an A/D converter circuit 50 and inputted into a frame memory 52 with synchronizing to a signal of a timing generator 51. The signal inputted into the frame memory 52 is converted to the video signal passed through a D/A converter circuit 53 and transmitted to a image change-over circuit 54. The image change-over circuit 54 receives a command signal from a control unit 60 by inputting an image change-over switch 61, so that a displayed-image on the display 55 is changed over to a photo-image by the CCD camera 26 and a photo-image by the CCD camera 16.

Reference numeral 56 is an image synthetic circuit for synthesizing displays of various information generated by a display circuit 57 and the photo-images by the CCD cameras 26 and 16 so as to display on the display 55.

The sectional image of the anterior part of the eye freezed-memorized by the frame memory 52 is transmitted to an image analyzing unit 200 passed through an interface circuit 64 by an input of an image transmittance switch 62.

(Image Analyzing Unit)

Reference numeral 201 is a computer unit for image-processing and analyzing the sectional image data inputted by the photographing unit 100 for a corneal section. The computer unit 201 comprises a frame memory for storing the image data and another memory for storing an analytic program for analyzing images described hereinafter in the inside of the computer unit 201. A keyboard 202 for inputting an operating instruction and a mouse 203 are connected with the computer 201. A personal computer of commercial items can be available instead of the hardware of the computer 201, the keyboard 202 and the mouse 203.

Reference numeral 204 is a colour display for displaying the sectional image, the analyzed result and the like inputted by the photographic unit 100 for a corneal section, and 205 is a video printer.

Next, it will be described herein as regards the operation of the above-mentioned structured apparatus.

After the eye to be examined is positioned at a predetermined position, the target plate 21 of the first alignment target projection optical system sharing with the fixation optical system 21 is fixated. The front image of the eye photographed by the CCD camera 26 is transmitted to the display 55 passed through the image change-over circuit 54. In order to form a predetermined relation between the first alignment target image and the reticle image displayed on the display 55, the operator shifts the photographing unit 100 for a corneal section up and down or left and right by handling a joystick not illustrated herein so as to achieve alignment. As a result of this process, it can be achieved to adjust the optical axis for the photographing unit 100 for a corneal section and the eye E. Also, by shifting the photographic unit 100 toward and away, the rough alignment of a working distance is performed so that the first alignment target image can be changed to the smallest and clearest one.

The adjustment of optical axis and the alignment of working distance are performed by observing the front image. Then, the display change-over switch 61 is pressed. The control unit 60 controls the image change-over circuit 54 by the command signal so as to change over the display-image of the display 55 to the photo-image by the CCD camera 16. The control unit 60 controls that the light source 27 for illuminating the anterior part of the eye is turned off and the light source 35 for the second alignment is turned on. When the second alignment target is projected onto the cornea of the eye by turning on the light source 35, and the target illuminaus flux reflected at adjacent the vertex of cornea is caught by the CCD camera 16 Therefore, the second alignment target image can be displayed on the display 55. Also, the aiming mark generated by the display circuit 57 is displayed with being overlapped with the photo-image by the image synthetic circuit 56.

The operator starts a detailed alignment so that the aiming mark and the second alignment target image can be formed to a desired positional relation.

When the alignment is completed, the flash lump 2 is turned on by pressing the photographic switch 62. The corneal section which is cut optically by the slit illumination light is photographed by the CCD camera 16. The control unit 60 controls that the photo-image is frozen into the frame memory 52 through the timing generator 51. The frozen image by the frame memory 52 is displayed on the display 55. In addition, the image may be desirable by using the image-forming lens for use in photomacrography 12. By using the image-forming lens for use in photomacrography 12, for example, an image which consists of corneal and anterior chamber can be obtained.

Next, the opacification condition is to be estimated by processing the obtained image. After the image analyzing unit 200 is set on condition that the image can be transmitted, the image transmittance switch 63 of the photographing unit 100 is pressed.

Figure 3:
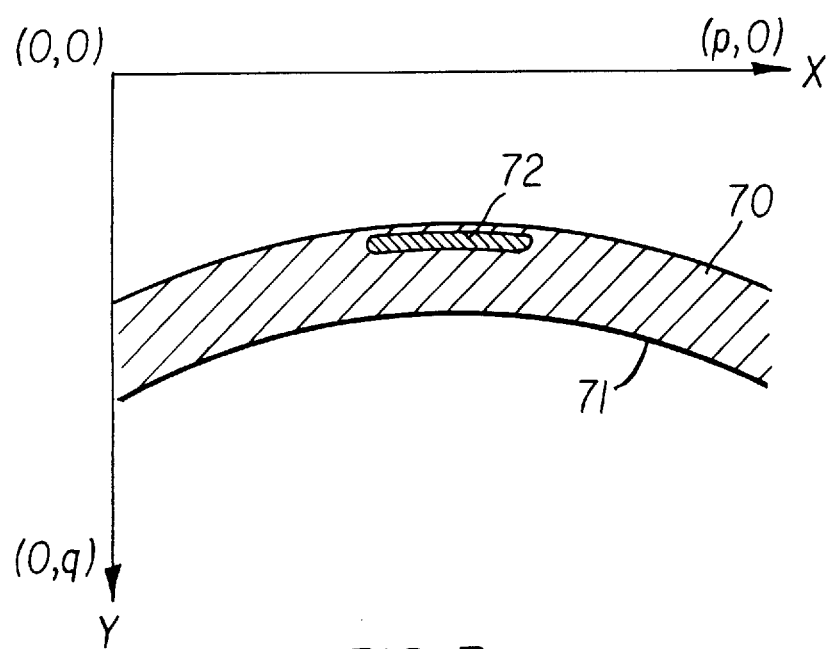
FIG. 3 is a view showing an image sample inputted by a frame memory of a computer unit 201 shown as in FIG. 2.

The frozen image by the frame memory 52 is output by the digital signal so that the image is inputted into the frame memory in the computer unit 201. Also, the inputted image by the frame memory is displayed on the color display 204. FIG. 3 is an image sample; 70 is a front side of cornea, 71 is a rear side of corneal, and 72 is a portion of opacification.

The operator inputs the command signal for analyzing an image by handling the mouse 203. The image analyzing unit 200 of the preferred embodiment comprises a first analyzing mode for performing up to the second step of analysis which will be describe later and displaying its result, and a second analyzing mode for performing up to the forth step of analysis and displaying its result. The operator follows the operating instructions which are displayed on the color display 204, and selects and inputs either analyzing mode. The image analyzing unit 200 starts to analyze and processes by following the selected analyzing mode.

The First Step of Analysis

First of all, corresponding to the sectional image inputted into the frame memory, assuming an axial direction of slit-light projection to be Y axial direction, and assuming a rectangular coordinate direction corresponding to the Y axial direction to be X axial direction. And, as shown in FIG. 3, assuming a left-up side on the frame memory to be the origin of X-Y coordinate axes,, the sectional image is positioned to the X-Y coordinate system. Also, since the sectional image has been inputted on the frame memory as digital image, a variable density of the photo-image can be obtained as a numerical value every 1 pixel (or every a certain range) of the X-Y coordinate system. In proportions as the numerical value increases, the density value will become high (for example, levels should be divided into 256 levels from 0 up to 225 levels). Therefore, an optional point A on the frame memory, A=(200, 150, 123), can be obtained by the X-Y coordinate and the density value.

The Second Step of Analysis

Secondly, by detecting the highest peak density value of Y axial direction every 1 pixel of X coordinate, Y coordinate corresponding to X coordinate can be obtained. By taking the above-mentioned process in order to find all X coordinates (or a certain interval), the peak density value and its Y coordinate points are obtained every X coordinate (1 PXL) so as to store the result into the memory.

In case that the first analyzing mode is selected, a image in FIG. 4 is displayed when the second step of analysis is completed. Based on the obtained result by the second step of analysis (the peak density value and its Y coordinate point every X coordinate), on the color display 204, each peak density point every X coordinate is marked, so that the marking points connected by line, a line 73, is displayed by being overlapped with the image of corneal section. The image of corneal section is displayed with a density of black-white, on the other hand the line 73 is displayed with a colored line. As a result of this, it is possible to see clearly the peak density point corresponding to a direction of thickness of corneal section. Further, a bar graph 74, indicated by a figure, is displayed below the screen by taking an ordinate for the peak density value every X coordinate.

By means of the above-mentioned display, the opacification point and its density at the corneal section can be caught visually, In addition, if necessary, the peak density value and its coordinate point may be displayed by the numerical value.

The Third Step of Analysis

In case that the second analyzing mode is selected, in succession to the second step of analysis a next step of analysis is executed. The peak density value and its Y coordinate point every X coordinate stored into the memory are extracted. On the Y coordinate point that the peak density value is obtained every each X coordinate for the whole of X coordinate (or a certain interval), from the basic point to a plus side and a minus side of Y axial direction, the density value for the interval, which is spaced per a predetermined pixel, is integrated (this analysis processing is called an integration of Y axial direction) so as to obtain each integration value every X coordinate.

Although only the peak density can be obtained every X coordinate in the second step of analysis, by integrating the density value at the direction of the corneal thickness, this step (the third step of analysis) can obtain the value including the opacification degree of the direction of corneal thickness. As a result of this, this step can be useful in estimating the accurate opacification condition, Due to this reason, it should be desirable for the integrated range of the density value by using the integration of Y axial direction to be a interval for including the whole of corneal section. This is set based on the relation of photographic magnification of the photographic unit 100 for a corneal section.

The Fourth Step of Analysis

By adding the integration value of Y axial direction every X coordinate obtained by the former steps, the integration value of the total density is obtained related to the photo-image of corneal section.

As following each step, the integration value of the total density can be the most suitable parameter for synthetically judging the variable density of the photo-image of corneal section. In addition, the opacification condition can be estimated quantitatively. Further, it is possible to estimate the opacification condition by use of the obtained value in each step of analysis.

FIG. 5 is a display sample showing an analyzed result in case of the second analyzing mode. As the same process of the first analyzing mode, based on the obtained result by the second step of analysis, the line 73 is displayed by being overlapped with the image of corneal section. Based on the obtained result by the third step of analysis, a bar graph 75, indicated by a figure, is displayed below the display by taking an ordinate for the value of the integration of Y axial direction every X coordinate (a way of taking an unit of the bar graph 75 is different from the bar graph 74 in FIG. 4). The value of the bar graph 75 includes the opacification degree of the direction of corneal thickness, therefore, more synthetic opacification condition can be estimated visually compared with the figure showing the peak density in FIG. 4.

Also, it is displayed on the screen that an integration value 76 denotes the integration value of the total density which is obtained by the fourth step of analysis.

By specifying the interval of X coordinate on the screen by using the mouse 203, the obtained value by the fourth step of analysis can be obtained as an added value to each integration value of the integration of Y axial direction within the specified interval.

When the above-mentioned display image is printed out and saved, a video printer 205 is operated to print out. Also, the analyzed result is stored into the memory device in the computer unit 201. When the time progressive change is estimated, the comparison and evaluation can be possible by lording the stored result.

Some various changes may be available to the above-mentioned preferred embodiment. In the preferred embodiment, the photo-image is a picture of cornea and anterior chamber. Since it is considered that a scattering light at the anterior chamber is more feeble than one at the cornea, the detecting of the peak density and the integrated condition have ranged up to the anterior chamber. However, by extracting only the corneal part, if the corneal part as a target is analyzed, more accurate value can be obtained.

In addition, since the alignment accuracy and processing speed are considered in the third step of analysis of the preferred embodiment, on the basis of such a Y coordinate point which is detected, some comparative wide range has been set for a processed range, But, if an apparatus can achieve the high accurate alignment, it can be possible to set the condition determinatively.

Further, the photographic optical system is not necessary for applying to an optical system based on the Scheipflug's principle.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for analyzing a section of an anterior part of an eye comprising:

input means for inputting a photographed image data of corneal section which is cut optically by a slit light;

image memory means for memorizing the image data of corneal section inputted by said input means;

image analyzing means for analyzing an optical density of the image of corneal section by processing the image data of corneal section memorized by said image memory means; and display means for displaying an analyzed result of said image analyzing means.

2. The ophthalmic apparatus according to claim 1, wherein said image analyzing means including:

first analyzing means for obtaining an optical density of each point by processing the image data of corneal section memorized by said image memory means; and second analyzing means for obtaining each peak optical density and its point of a first axial direction alongside of a projection axis of said slit light based on the optical density obtained by said first analyzing means.

3. The ophthalmic apparatus according to claim 1, wherein said image analyzing means including:

first analyzing means for obtaining the optical density of each point by processing the image data of corneal section memorized by said image memory means; and second analyzing means for obtaining each peak optical density and its point of a first axial direction alongside of a projection axis of said slit light based on the optical density obtained by said first analyzing means, whereby the point of peak optical density obtained by said second analyzing means being marked and displayed by said display means by being overlapped with the image of corneal section.

4. The ophthalmic apparatus according to claim 1, wherein said image analyzing means including:

analyzing means for obtaining the optical density of each point by processing the image data of corneal section memorized by said image memory means; and integrating means for integrating the optical density of the axial direction alongside of the projection axis of said slit light based on the optical density obtained by said analyzing means.

5. The ophthalmic apparatus according to claim 1, wherein said image analyzing means including:

analyzing means for obtaining the optical density of each point by processing the image data of corneal section memorized by said image memory means; and means for integrating the optical density of the axial direction alongside of the projection axis of said slit light based on the optical density obtained by said analyzing means, whereby an integrated value obtained by said integrating means being graphically displayed by said display means.

6. The ophthalmic apparatus according to claim 1, wherein said image analyzing means including:

analyzing means for obtaining the optical density of each point by processing the image data of corneal section memorized by said image memory means; and second integrating means for integrating the optical density of a predetermined range based on the optical density obtained by said analyzing means.

7. An ophthalmic apparatus for analyzing a section of an anterior part of an eye providing a photographing unit for a corneal section and an image analyzing unit comprising:

a photographic unit including at least slit projection optical system for projecting a slit image onto an eye to be examined; and slit-section photographing optical system for photographing an optical sectional image of the slit image which is projected onto the eye to be examined by said slit projection optical system;

an image analyzing unit including input means for inputting the image data of a section of an anterior part of an eye photographed by said slit-section photographing optical system;

first analyzing means for analyzing a point coordinate and an optical density of a direction which intersects on a slit-light projection optical axis of the slit photo-image of the eye to be examined photographed by said slit-section photographing optical system based on the image data of the section of the anterior part of the eye which is inputted by said input means; and second analyzing means for analyzing the peak optical density and its point coordinate of the axial direction of the slit-light projection of said slit-light photo-image.

8. The ophthalmic apparatus according to claim, 7 further comprising display means for displaying an analyzed result by said first analyzing means and said second analyzing means.

9. The ophthalmic apparatus according to claim 8, wherein said display means displays a point of peak optical density at each point coordinate of the direction which intersects on the slit-light projection axis analyzed by said first analyzing means with a marking indication by being overlapped with the image of corneal section.

10. The ophthalmic apparatus according to claim 9, wherein said display means further displays a bar graph so that a value of the peak optical density of the axial direction of the slit-light projection which is analyzed by said second analyzing means corresponds to the point coordinate of the direction which intersects on said slit-light projection optical axis.

11. The ophthalmic apparatus according to claim 7, further comprising memory means for memorizing the analyzed result by said first analyzing means and said second analyzing means.

12. The ophthalmic apparatus according to claim 7, further comprising integrating means for integrating the optical density of the axial direction of the slit-light projection based on the value of the peak density at each coordinate point of the direction which intersects on the slit-light projection axis obtained by said first analyzing means and said second analyzing means.

13. The ophthalmic apparatus according to claim 12, further comprising calculating means for obtaining an integrated value of a total density of the image of the section of the anterior part of the eye based on the integrated value of optical density of the axial direction of slit-light projection at each coordinate position of direction which intersects on the slit-light projection axis obtained by said integrating means.

14. The ophthalmic apparatus according to claim 13, further comprising display means for displaying an obtained result by said integrating means and said calculating means.

15. The ophthalmic apparatus according to claim 14 wherein said display means displays the bar graph so that a integrated value of optical density of the axial direction of slit-light projection obtained by said integrating means and said calculating means corresponds to the point coordinate of the direction which intersects on the axis of slit-light projection.

16. The ophthalmic apparatus according to clan 13, further comprising memory means for memorizing the obtained result by said calculating means.

* * * * *